US00PP25111P2

(12) United States Plant Patent
Kako

(10) Patent No.: US PP25,111 P2
(45) Date of Patent: Nov. 25, 2014

(54) ***CATHARANTHUS* PLANT NAMED 'SUNNICHILAVE'**

(50) Latin Name: *Catharanthus roseus*
Varietal Denomination: Sunnichilave

(71) Applicant: Tetsuya Kako, Shimane (JP)

(72) Inventor: Tetsuya Kako, Shimane (JP)

(73) Assignee: Suntory Flowers Ltd., Tokyo (JP)

( * ) Notice: Subject to any disclaimer, the term of this patent is extended or adjusted under 35 U.S.C. 154(b) by 87 days.

(21) Appl. No.: 13/815,119

(22) Filed: Jan. 31, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — C. A. Whealy

(57) ABSTRACT

A new and distinct cultivar of *Catharanthus* plant named 'Sunnichilave', characterized by its trailing plant habit; vigorous growth habit; freely basal branching habit; freely flowering habit; long flowering period; relatively large lavender-colored flowers; and good garden performance.

1 Drawing Sheet

Botanical designation: *Catharanthus roseus.*
Cultivar denomination: 'SUNNICHILAVE'.

BACKGROUND OF THE INVENTION

The present invention relates to a new and distinct *Catharanthus* plant, botanically known as *Catharanthus roseus* and hereinafter referred to by the name 'Sunnichilave'.

The new *Catharanthus* plant is a product of a planned breeding program conducted by the Inventor in Higashiomi, Shiga, Japan. The objective of the breeding program is to develop new freely branching and vigorous *Catharanthus* plants with trailing plant habit and numerous attractive flowers.

The new *Catharanthus* plant originated from a cross-pollination conducted by the Inventor in Higashiomi, Shiga, Japan in June, 2006 of a proprietary selection of *Catharanthus roseus* identified as code number Casp5-1, not patented, as the female, or seed, parent with a proprietary selection of *Catharanthus roseus* identified as code number 03-20-1, not patented, as the male, or pollen, parent. The new *Catharanthus* plant was discovered and selected by the Inventor as a single flowering plant from within the progeny of the stated cross-pollination in a controlled greenhouse environment in Higashiomi, Shiga, Japan in April, 2007.

Asexual reproduction of the new *Catharanthus* plant by vegetative cuttings in a controlled greenhouse environment in Higashiomi, Shiga, Japan since April, 2007 has shown that the unique features of this new *Catharanthus* plant are stable and reproduced true to type in successive generations.

SUMMARY OF THE INVENTION

Plants of the new *Catharanthus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunnichilave'.

These characteristics in combination distinguish 'Sunnichilave' as a new and distinct *Catharanthus* plant:

1. Trailing plant habit.
2. Vigorous growth habit.
3. Freely basal branching habit.
4. Freely flowering habit.
5. Long flowering period.
6. Relatively large lavender-colored flowers.
7. Good garden performance.

Plants of the new *Catharanthus* can be compared to plants of the female parent selection. Plants of the new *Catharanthus* differ primarily from plants of the female parent selection in the following characteristics:

1. Plants of the new *Catharanthus* are more trailing than and not as upright as plants of the female parent selection.
2. Plants of the new *Catharanthus* and the female parent selection differ in flower color as plants of the female parent selection have pink-colored flowers.

Plants of the new *Catharanthus* can be compared to plants of the male parent selection. Plants of the new *Catharanthus* differ primarily from plants of the male parent selection in the following characteristics:

1. Plants of the new *Catharanthus* and the male parent selection differ in lateral branch color as plants of the male parent selection have green-colored lateral branches.
2. Plants of the new *Catharanthus* and the male parent selection differ in flower color as plants of the male parent selection have white-colored flowers.

Plants of the new *Catharanthus* can be compared to plants of the *Catharanthus roseus* 'Sunnichipink', disclosed in U.S. Plant Pat. No. 20,523. In side-by-side comparisons conducted in Higashiomi, Shiga, Japan, plants of the new *Catharanthus* differed from plants of 'Sunnichipink' in the following characteristics:

1. Plants of the new *Catharanthus* were taller than plants of 'Sunnichipink'.
2. Plants of the new *Catharanthus* had longer internodes than plants of 'Sunnichipink'.

3. Plants of the new *Catharanthus* and 'Sunnichipink' differed in lateral branch color as plants of 'Sunnichipink' have green-colored lateral branches.
4. Plants of the new *Catharanthus* had larger leaves with longer petioles than plants of 'Sunnichipink'.
5. Flowers of plants of the new *Catharanthus* were round in overall shape whereas flowers of plants of 'Sunnichipink' were star-shaped.
6. Plants of the new *Catharanthus* had smaller flowers than plants of 'Sunnichipink'.
7. Plants of the new *Catharanthus* and 'Sunnichipink' differed in flower color as plants of 'Sunnichipink' had large light red purple-colored flowers with darker red purple-colored centers.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet comprises a side perspective view of a typical flowering plant of 'Sunnichilave' grown in a container.

The photograph at the bottom of the sheet comprises a close-up view of a typical flowering plant of 'Sunnichilave'.

DETAILED BOTANICAL DESCRIPTION

The aforementioned photographs and following observations, measurements and values describe plants grown during the winter in 15-cm containers in a polyethylene-covered greenhouse in Higashiomi, Shiga, Japan and under cultural practices typical of commercial production. During the production of the plants, day temperatures averaged 25° C. and night temperatures averaged 15° C. Plants were four months old when the description and photographs were taken. In the following description, color references are made to The Royal Horticultural Society Colour Chart, 2007 Edition, except where general terms of ordinary dictionary significance are used.

Botanical classification: *Catharanthus roseus* 'Sunnichilave'.

Parentage:

*Female, or seed, parent*.—Proprietary selection of *Catharanthus roseus* identified as code number Casp5-1, not patented.

*Male, or pollen, parent*.—Proprietary selection of *Catharanthus roseus* identified as code number 03-20-1, not patented.

Propagation:

*Type*.—By vegetative cuttings.

*Time to initiate roots, summer*.—About two weeks at 30° C.

*Time to initiate roots, winter*.—About three weeks at 25° C.

*Time to produce a rooted young plant, summer*.—About five weeks at 30° C.

*Time to produce a rooted young plant, winter*.—About six weeks at 25° C.

*Root description*.—Fibrous; white in color.

*Rooting habit*.—Freely branching; medium density.

Plant description:

*Plant and growth habit*.—Trailing plant habit; freely basal branching habit with numerous lateral branches developing per plant; vigorous growth habit.

*Plant height*.—About 12 cm.

*Plant diameter*.—About 36.8 cm.

Lateral branch description:

*Length*.—About 34.1 cm.

*Diameter*.—About 3.1 mm.

*Internode length*.—About 2.1 cm.

*Strength*.—Strong.

*Aspect*.—Upright to outwardly.

*Texture*.—Sparsely pubescent.

*Color*.—Close to 60A.

Foliage description:

*Arrangement*.—Opposite, simple.

*Length*.—About 7.1 cm.

*Width*.—About 3.3 cm.

*Shape*.—Narrowly elliptic.

*Apex*.—Obtuse.

*Base*.—Obtuse.

*Margin*.—Entire.

*Texture, upper surface*.—Smooth, glabrous.

*Texture, lower surface*.—Sparsely pubescent.

*Venation pattern*.—Pinnate; reticulate.

*Color*.—Developing leaves, upper surface: Close to 143A. Developing leaves, lower surface: Close to 144A. Fully expanded leaves, upper surface: Close to 138A; venation, close to 144D. Fully expanded leaves, lower surface: Close to 143B; venation, close to 144D.

*Petioles*.—Length: About 5 mm. Diameter: About 1.1 mm. Texture, upper and lower surfaces: Sparsely pubescent. Color, upper and lower surfaces: Close to 61B.

Flower description:

*Flower arrangement and habit*.—Single round salver-form flowers arising from upper leaf axils; freely flowering habit with usually about 13 flowers developing per plant; flowers face upright or outwardly. Fragrance: None detected.

*Flowering habit*.—Plants begin flowering about two to three weeks after planting; long flowering period, in the garden, plants flower continuously from the early summer to late autumn in Japan;

*Flower longevity*.—Individual flowers last about two to three days on the plant; flowers not persistent.

*Flower diameter*.—About 4.1 cm.

*Flower length (depth)*.—About 3.9 cm.

*Tube length*.—About 2.9 cm.

*Tube diameter, at the base*.—About 1.4 mm.

*Flower buds*.—Length: About 3.7 cm. Diameter: About 5.3 mm. Shape: Cylindrical. Color: Close to 62D.

*Corolla*.—Arrangement: Five petals in a single whorl fused at the base into a tube. Petal length from throat: About 1.9 cm. Petal width: About 2 cm. Petal shape: Broadly obovate. Petal apex: Mucronate. Petal margin: Entire; slightly undulate. Petal texture, upper and lower surfaces: Smooth, glabrous; velvety. Throat texture: Smooth, glabrous. Tube texture: Smooth, glabrous. Color: Petal, when opening and fully opened, upper surface: Close to 75B; towards the throat, close to NN155B. Petal, when opening and fully opened, lower surface: Close to 76D. Throat: Close to 145C. Tube: Close to 150C.

*Calyx*.—Arrangement: Star-shaped tubular calyx with five sepals fused towards the base. Sepal length: About 4.1 mm. Sepal width: About 1.1 mm. Sepal shape: Lanceolate. Sepal apex: Acute. Sepal margin: Entire. Sepal texture, upper and lower surfaces: Sparsely pubescent. Color, immature and mature, upper surface: Close to 143B. Color, immature and mature, lower surface: Close to 143B.

*Peduncles*.—Length: About 4.1 mm. Diameter: About 1.7 mm. Angle: Upright to outwardly. Strength: Strong. Texture: Smooth, glabrous. Color: Close to 145B.

*Reproductive organs*.—Stamens: Quantity per flower: Five. Stamen length: About 3.5 mm. Anther shape: Narrowly elliptic. Anther size: About 1.5 mm by 3.3 mm. Anther color: Close to 9D. Pollen amount: Moderate. Pollen color: Close to 10D. Pistils: Quantity per flower: One. Pistil length: About 2.5 cm. Style color: Close to 145C. Stigma shape: Transversely ellipsoidal. Stigma color: Close to 145A. Ovary color: Close to 145A. Seeds and fruits: Seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: Plants of the new *Catharanthus* have not been observed to be resistant to pathogens and pests common to *Catharanthus* plants.

It is claimed:

1. A new and distinct *Catharanthus* plant named 'Sunnichilave' as illustrated and described.

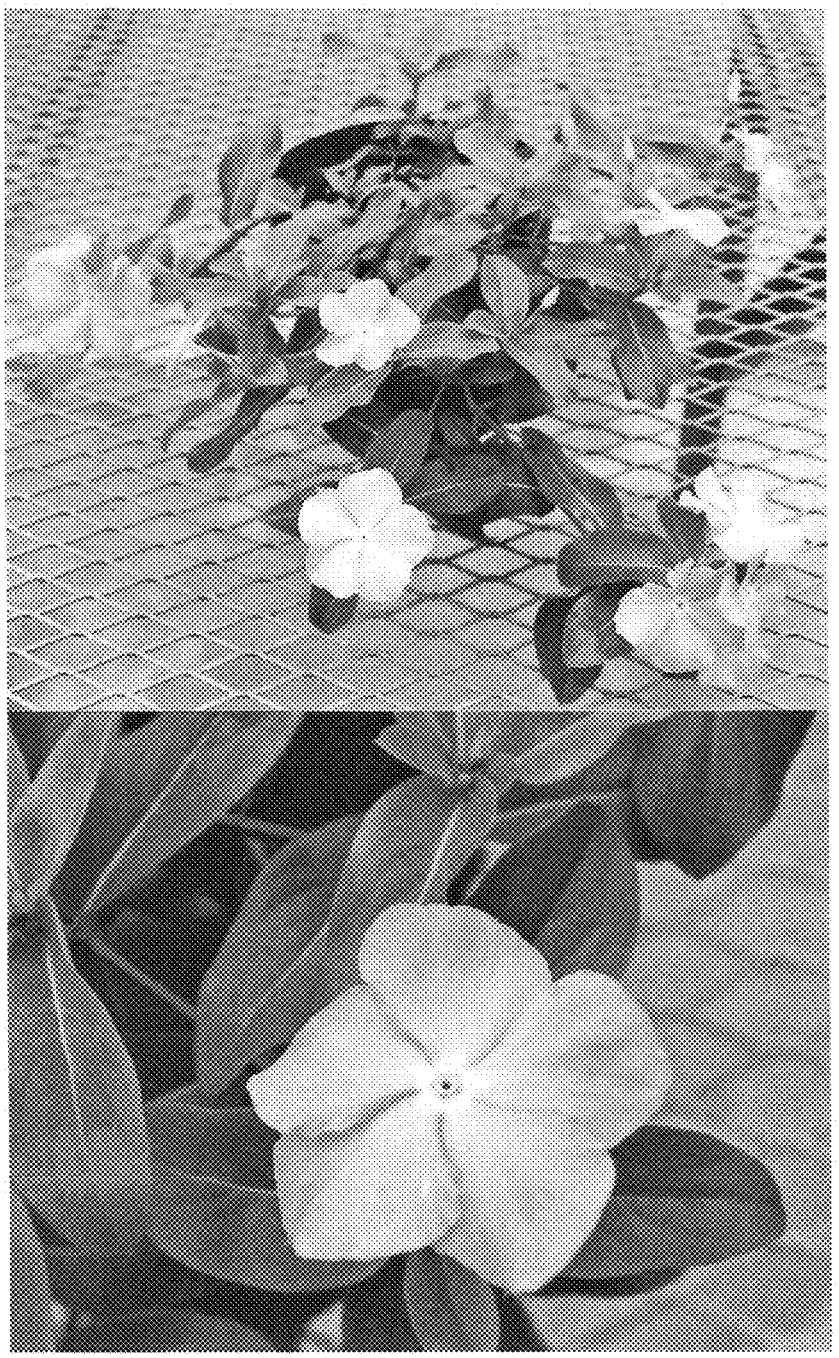

* * * * *